United States Patent
Kennedy

(10) Patent No.: US 6,429,211 B1
(45) Date of Patent: Aug. 6, 2002

(54) PRAZIQUANTEL COMPOUNDS FOR TREATING DISEASES DUE TO SARCOCYSTIS NEOSPORA TOXOPLASMA AND ISOSPORA

(75) Inventor: Thomas J. Kennedy, Mission, KS (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/576,791

(22) Filed: May 23, 2000

(51) Int. Cl.⁷ .................................................. A61K 31/47
(52) U.S. Cl. ........................................................ 514/308
(58) Field of Search .......................................... 514/308

(56) References Cited

U.S. PATENT DOCUMENTS

| | | | |
|---|---|---|---|
| 4,001,411 A | 1/1977 | Seubert et al. | 424/250 |
| 4,447,414 A | 5/1984 | Gay et al. | 424/81 |
| 4,933,341 A | 6/1990 | Lindner et al. | 514/241 |
| 4,935,423 A | 6/1990 | Lindner et al. | 514/242 |
| 5,114,938 A | 5/1992 | Lindner et al. | 514/242 |
| 5,141,938 A | 8/1992 | Lindner et al. | 514/242 |
| 5,188,832 A | 2/1993 | Mehlhorn et al. | 424/405 |
| 5,196,562 A | 3/1993 | Lindner et al. | 558/404 |
| 5,256,631 A | 10/1993 | Lindner et al. | 504/229 |
| 5,464,837 A | 11/1995 | Mehlhorn et al. | 514/242 |
| 5,663,155 A | 9/1997 | McCaffrey et al. | 514/45 |
| 5,824,653 A | 10/1998 | Beuvry et al. | 514/30 |
| 6,051,604 A * | 4/2000 | Fitzgerald | 514/503 |

* cited by examiner

Primary Examiner—Kevin E. Weddington
(74) Attorney, Agent, or Firm—Joseph C. Gil; Godfried R. Akorli

(57) ABSTRACT

Disclosed herein are compositions and methods of treating therapeutically, or metaphylactically infected mammals susceptible to, or infected mammals suffering from parasitic neurologic or abortigenic diseases such as Sarcocystis, Neosporosis or Toxoplasmosis or Isosporosis that are treatable with a praziquantel compound by administering thereto a composition containing a pharmaceutically effective amount of praziquantel or derivative thereof, including metaphylactic and single high dose treatment regimens.

14 Claims, No Drawings

PRAZIQUANTEL COMPOUNDS FOR TREATING DISEASES DUE TO SARCOCYSTIS NEOSPORA TOXOPLASMA AND ISOSPORA

FIELD OF THE INVENTION

Field of the Invention: The present invention relates to a praziquantel composition for treating animals infected with parasites that cause abortigenic or neurologic diseases. More specifically, the present invention relates a praziquantel composition that is useful in treating parasitic protozoa such as coccidia that cause abortigenic or neurologic diseases of mammals.

Brief Description of the Prior Art: In protecting and treating various mammals, insects and fish from diseases caused by protozoa suspected of causing neurologic and/or abortigenic diseases, the art has used a number of compounds, recent among which are triazineone compounds. Generally, protozoa that are sensitive to these compounds include parasites that infect the intestines of birds, mammals and insects causing diarrhea, wasting disease, nausea and vomiting. Recently it has been found that some parasites that pass through the blood brain barrier, as well as parasites that pass through the placental barrier can be treated with the triazineones. Illustrative of parasites that are now known to cross the blood brain barrier or the placental barrier are those causing coccidial diseases such as *Toxoplasma gondii, Sarcocystis neurona, Neospora caninum, Neospora hugesii,* and *Isospora suis.* Illustrative of the triazineone compounds are triazinediones such as diclazuril compounds, and triazinetriones such as toltrazuril compounds. See U.S. Pat Nos. 4,933,341; 4,935,423; 5,114,938; 5,141,938; 5,188,832; 5,196,562; 5,256,631 and 5,464,837.

While other art-related compounds pertinent among which is praziquantel (2-acyl-4-oxo-hexahydro-4H-pyrazino[2,1-a[isoquinoline derivatives) are disclosed for use in treating parasites, the disclosure lacks any teaching or suggestion relating to the compounds as being useful in treating parasites that cross the blood or placental barrier. Generally, praziquantel has been used by itself or in combination with other compounds to formulate anthelmintic compositions for treating infestation of cestodes and nematodes and the like. See U.S. Pat. No. 4,001,411, 4,447,414, and 5,824,653.

U.S. Pat. No. 5,663,155 discloses praziquantel for use in the prevention and treatment of parasitic infections, which cause diseases such as malaria, trypanosomiasis, leishmania, schistosomiasis and elephantitis. The patent also suggests that praziquantel could be used to treat parasitic infections limited to the blood, lymph and tissues. Toxoplasmosis and Sarcocystis are specifically mentioned in the context of their infection of muscle tissues or intestines. There is no mention of treatment or prevention of diseases wherein the Toxoplasma, Sarcocystis, Neospora or Isospora is embedded into the brain of adult mammals or passed through the placental barrier to infect central nervous tissues of the fetus, producing abortion or weak newborns.

Generally, the mode of action of the triazineones is to attack the intermediate parasite stages found in the gut and intestinal wall cells, causing the endoplasmic reticulum, the perinuclear space and the mitochondria of the parasite to swell. This purportedly disturbs the ability for nuclear divisions causing the schizonts and microgamonts to remain small, forming only a few merozoites and microgametes respectively. The end result is reported to be the loss of the ability of these latter stages of the parasites to penetrate new mammalian cells, effectively halting the replication of the parasite in the host.

The mode of action of paraziquantel, as disclosed by U.S. Pat. No. 5,663,155 (ibid.), is related to the disruption of enzymatic processes of the parasite that relate to the metabolism of purine derivatives and purine-like chemical structures. Parasites are acutely sensitive to interference of these processes, thus compositions that specifically target these processes can be used to selectively eliminate a parasitic infection. Praziquantel is administered so as to attack parasites that are related to muscle tissue, intestine or blood infection. There is no mention of treating parasites of the central nervous system (brain and spinal cord) or parasites that can pass the placental barrier.

While the art has been concerned with protozoa suspected of causing neurologic and/or abortigenic diseases of mammals since the 1970s, successful isolation and in vitro cultivation of some of these protozoa proved to be difficult. For example, successful isolation of parasites from the brain or cerebral spinal fluid was not accomplished until the late 1980s. However, once it was determined that neurologic diseases could be produced by protozoa infecting the brain, and abortigenic diseases could be produced by protozoa infecting the fetus, there was a need for effective anti-protozoa drugs which could cross the blood-brain barrier and the placental barrier without producing deleterious side effects. Very few drugs are able to pass the blood-brain barrier or the placental barrier of mammals. Unfortunately, many of the art-known drugs that do cross the blood-brain barrier and/or the placental barrier to effectively treat parasitic infections of the brain have detrimental side effects such that they cannot be used without great risk. Therefore, there have been no effective drugs approved to date which provide an effective treatment for such neurologic or abortigenic diseases.

It is noteworthy that based on the disclosed mode of action of praziquantel in U.S. Pat. No. 5,663,155, relative to its broad attack on enzymes which affect purine metabolism, one would have expected that this compound might also produce deleterious effects if used to treat mammals with parasitic brain infections.

The following is a brief description of the parasitic diseases of the immediate invention, which are treatable with praziquantel. Equine Protozoal Myeloencephalitis (EPM) is a neurologic disease of horses, with a predilection for young horses undergoing stress (e.g. thoroughbred racehorses and purebred performance horses), and is thus a disease with significant monetary impact for the horse industry. EPM, first recognized as a disease in the 1970s, was not cultured from a horse with EPM and given the name *Sarcocystis neurona* until 1991. In 1997, a Neospora spp., now named *Neospora hugesi,* was isolated from the brain of a horse with EPM. Accordingly, it is now proposed that EPM may be caused by this newly recognized organism alone, by *Sarcocystis neurona* alone or the combination of the two.

Another coccidial parasite, *Toxoplasma gondii,* has been known for some time and was first isolated from the intestines and muscle tissue of cats. The definitive host for this parasite is the cat that can harbor the organism for long periods of time spreading oocysts to other animals including bovines, ovines, porcines and humans. Infection of sheep, cattle and humans has been associated with abortion and congenitally acquired disorders, which primarily affect the central nervous system. It has also recently been associated with abortion and malformation in kittens born to infected queens that had been seronegative prior to infection during pregnancy. Non-feline hosts such as bovines, ovines, porcines and humans do not produce oocysts but develop and may suffer from invasion of muscle and brain by tachyzoites and bradyzoites which produce the clinical signs of disease—neurological symptoms and abortion with fetal defects. It has been reported that 60% of cats are serologically positive to *T. gondii*. Once again, there is no approved treatment or prophylactic for toxoplasmosis.

Yet another coccidial parasite, *Neospora caninum* which was first isolated from dogs in 1988, produces both a neurologic and abortigenic disease in animals. It was previously confused with *Toxoplasma gondii*. The disease caused by this parasite occurs most severely in transplacentally infected puppies and is characterized by progressive ascending paralysis in the puppies, particularly of the hind limbs; polymyositis and hepatitis may also occur. This disease has more recently been recognized as a major cause of abortion and neurologically associated limb defects in newborn calves. Microscopic lesions of non-suppurative encephalitis and myocarditis in aborted fetuses may be seen in the brain, spinal cord and heart. A definitive host for *Neospora caninum* has recently been identified to be the dog. At this time there is no approved treatment or prophylaxis for either *Neospora caninum* of dogs or bovines or *Neospora hugesi* of horses.

As would be gathered from the foregoing, the prior art, including the above-cited references do not suggest or teach the use of praziquantel in treating animals infected with coccidia or, more specifically, of the family Sarcocystidae causing abortigenic or neurologic diseases without causing intolerable side effects. By the present invention, there is provided an improved and safe treatment for animals afflicted with parasitic diseases manifesting as neurologic or abortigenic diseases.

SUMMARY OF THE INVENTION

In accordance with the foregoing, the present invention encompasses a composition and a method of therapeutically treating a diseased animal suffering from a parasitic neurologic or abortigenic disease that is susceptible to being treated with a pharmaceutically effective amount of praziquantel. The method comprises administering to the animal a pharmaceutically effective amount of praziquantel.

The term "pharmaceutically-effective amount" as used herein means that the amount of praziquantel or a derivative thereof being administered is sufficient to inhibit the in vivo or in vitro growth of the parasitic protozoa, without causing adverse reactions in the mammal being treated. Typically the parasitic protozoa are coccidia that produce neurological disease and/or abortions. The pharmaceutically-effective amount controls the parasites in the infected tissues; consequently, the animal's health improves. Moreover the pharmaceutically effective amount is neurologically-effective or placentally-effective in that the praziquantel or derivative thereof is in an amount that is able to cross the blood brain barrier to treat parasites infecting the central nervous system, or placental barrier without causing adverse reactions in the mammal being treated.

Further, the present invention encompasses a method of metaphylactically treating an animal infected with a parasite that can cause a neurologic or abortigenic disease that is susceptible to being treated with praziquantel. The metapylactic treatment comprises administering to the animal the praziquantel using a metaphylactically-effective regimen. By the term "metaphylactically-effective regimen" is meant administering scheduled intermittent doses of a praziquantel compound or a derivative thereof for a prolonged period until said animal overcomes the invading parasites by, say, developing a protective immune response or otherwise clearing the parasite. Typically, the regimen is such as would effectively control the parasites and prevent clinical signs of disease. The metaphylactically-effective dose can also be administered for a prolonged period up to five years or the lifetime of the animal, especially in instance when the parasite is difficult to control.

Also, the present invention encompasses a single high dose treatment of the animals. This method comprises administering to the animals a single high dose of a pharmaceutically effective amount of praziquantel to a diseased animal suffering from a parasitic neurologic or abortigenic disease that is susceptible to being treated with a praziquantel compound or derivative thereof. By the term "single high dose" is meant an amount that is administered only once to control the disease-causing parasites. This amount is significantly higher than the dose amount employed in the therapeutic or metapylactic treatment and is effective in controlling the disease-causing parasites, and as such would not result in detrimental effects such as toxicity. The single high dose of praziquantel is accordingly greater than 10 mg/Kg. This and other aspects of the invention are described more fully hereunder.

DETAILED DESCRIPTION OF THE INVENTION

As set forth above, the present invention relates to a composition for, or method of treating an infected or diseased mammals suffering from a parasitic disease that manifests as neurologic or abortigenic disease that is susceptible to being treated with a praziquantel compound or derivative thereof. The method comprises administering to the mammal a composition containing a pharmaceutically effective amount of praziquantel. Illustrative but non-limiting examples of the animals can be equines, bovines, felines, canines, swine, ovines, birds, insects and humans. The parasites infecting or causing disease are coccidia of the Family Sarcocystidae that can manifest as neurologic or abortigenic diseases. Illustrative but non-limiting examples thereof can be selected from the group consisting of Sarcocystis spp., Neospora spp. and Toxoplasma spp. The Sarcocystidae are typically selected from the group consisting of *S. neurona, N. hugesi, N. caninum* and *T. gondii*. The protozoan infections or diseases include but are not limited to EPM, Neosporosis, and Toxoplasmosis.

In the practice of the invention, treatment of the parasitic infections or diseases caused by the protozoa described herein results in the alleviation of the symptoms of the neurologic and abortigenic diseases. Generally, the symptoms include lameness, ataxia, paralysis, abortion, weak newborns and other related disorders. For the therapeutic treatment, animals already suffering the above signs of disease are treated with the praziquantel compound. Typically the duration of treatment is from about 28 days to 90 days and preferably from about 28 to 60 days. It is understood that for therapeutic treatment, the treatment regimen can be administered once a day, two or more times a day, once every other day or even once per week, depending on factors such as the severity of the disease and the type of disease-producing parasite. In some cases, however, the treatment regimen can last indefinitely, sometimes for the remaining life of the animal. The latter treatment regimen would be required in the case of infection of an animal with a more resistant strain of parasite. However, the treatment can be extended for longer periods of time as necessary until the signs of disease are eliminated. The preferred treatment is once daily for about 28 days. The preferred dose for treatment ranges from 1 mg/Kg to 100 mg/Kg, preferably from 2.5 mg/Kg to 25 mg/Kg.

For the metaphylactic treatment, animals that are infected are treated to protect them against clinical manifestation of diseases. This treatment eventually results in the animals' acquisition of the ability to control the parasite, say, by the establishing an effective immune response to impart protection against future infections, without a need for further administration of praziquantel. The metaphylactic activity, in accordance with the invention, refers to the use of the praziquantel compounds on a scheduled intermittent treatment regimen (metaphylactically-effective regimen) to control the protozoa, which may have infected the animal since the previous treatment. Accordingly, the metaphylactically-effective regimen is administered to reduce their ability to cause disease by, say, killing them or reducing them in number. In essence, the metaphylactically effective regimen can be administered about once per month, over the lifetime of the animal or until an inherent clearance mechanism, e.g., an effective immune response, develops within the animal to protect it from future infections. The latter can occur within 5 years or less. As would be realized, the metaphylactic treatment is based on the recognition that when animals are infected with the protozoa described herein, they do not demonstrate clinical signs such as neurological signs or abortion until a significant time has passed (e.g., 2–6 months post infection). In contrast, the enteric protozoan infections manifest themselves shortly after infection. In accordance with this invention, the metaphylactic treatment prevents the parasite from establishing itself and causing a clinical disease. The treatment regimen is on an intermittent schedule of about once per month, once per two months or once per two weeks at a dose equivalent to about between 1.0 and 100 mg/Kg, preferably about 1.0 to 25 mg/Kg and more preferably about 2.5 to 10 mg/Kg. The high range would be required in particularly resistant cases (e.g., when an animal is infected with a resistant strain). The required dose level and duration of treatment are within the purview of one of ordinary skill in the art. A preferred treatment regimen for horses with EPM or bovines and dogs with Neosporosis is about 1.0 to 25 mg/Kg, and a more preferred range is about 2.5 to 10 mg/Kg of praziquantel or derivatives thereof every 28 days.

For the single high dose treatment praziquantel is administered in pharmaceutically effective amounts that are greater than 10 mg/Kg and up to about 100 mg/Kg. It is a distinct feature of the invention that the compounds of this invention can be non-toxic, thus they can be administrated at high dose levels. The advantage of the high dose administration resides in the fact that repeated doses are not required.

Without being bound to any particular theory of the invention, it is believed that the unexpected success of the treatments described herein results from the ability of praziquantel to cross the blood-brain barrier or placental barrier. It is believed that the compounds of this invention easily cross the blood-brain barrier and, also, are able to penetrate the placenta and kill the protozoa in situ in the brain and cerebral spinal fluid/spinal cord. It has further been found that the compounds of this class are non-toxic and non-mutagenic even at the high doses necessary for the single high dose treatment regimen described herein.

Heretofore, no cost-effective, easily administered drugs have been available for effectively treating and protecting against these diseases without producing unacceptable side effects such as toxicity or mutagenicity in mammals.

In the practice of the invention, praziquantel can be formulated in any convenient manner for administration to animals. Formulations suitable for oral administration, which is preferred herein, can be suspensions, tablets, capsules, gels, pastes, boluses, or preparations in the form of powders, granules, or pellets. The more preferred orally administered formulation is in the form of a paste or a feed additive. Other modes of administration that can be employed including parenteral, topical, intramuscular, and intramucosal or by other routes known to those skilled in the art. Topical administration in the form of a pour-on is also preferred.

Typically, pharmaceutically acceptable carriers and auxiliaries are employed in the formulations. Examples thereof can be a thickening agents selected from the group consisting of Carbopol; inorganic thickeners such as silicates, bentonites or colloidal silica; organic thickeners such as fatty alcohols or fatty acid esters and wetting agents selected from the group consisting of polyethylene glycol and sodium lauryl sulfate with Carbopols. Preferred herein as thickening agents for paste formulations are Carbopol 974P and Carbopol 934P. Also employed herein can be preservatives selected from the group consisting of parabens, alcohols and aldehydes. These may be liquid, solid, or gaseous materials, which are otherwise inert or medically acceptable and are compatible with the active ingredients.

Surprisingly, the pastes, according to the invention, are effective when used in treating the parasites. More specifically, it is surprising that the pastes of the present invention are deliverable in a neurologically-effective dose. They are effective in delivering the praziquantel to cross the blood-brain or placenta barrier and attack the parasites that have already invaded the brain or infected the fetus of a pregnant animal. As a matter of convenience, there is provided herein a description of a specific embodiment of the pastes preferred herein and how it is prepared. A preferred paste, according to the present invention contains a micronized suspension of the praziquantel, propylene glycol, a thickening agent such as Carbopol, preservatives such as Methylparaben and Propylparaben, and water. The paste can be made by combining water, typically, purified water and Propylene Glycol, heating the combination to about 70° C., and adding the preservatives, at this temperature. The resulting mixture is cooled to room temperature after which Carbopol, preferably in the form of Carbopol 974P or 934P, is added. Finally the praziquantel is added. After complete mixing, the pH is adjusted to approximately 6.0 with sodium hydroxide. The most preferable paste includes 15% w/w Praziquantel, 20% w/w Propylene Glycol, 0.5% w/w Carbopol 974P, 0.14% w/w Methylparaben, 0,02% w/w Propylparaben, 0.1% w/w sodium hydroxide with the remainder being purified water. Sweeteners including dextrose, sucrose, lactose, fructose, sorbitol, xylitol, artificial sweeteners and molasses may be added to improve palatability. Additionally, yeast or liver flavoring may be added for the same purpose.

The invention is further described by following illustrative but non-limiting examples.

EXAMPLE 1

In order to determine the scope of protection provided by praziquantel, in vitro testing was conducted. *Sarcocystis neurona* was evaluated for its sensitivity to this compound. Strain SN3 of *Sarcocystis neurona* was used. Praziquantel was tested at two concentrations, 10 μg/mL and 20 μg/mL.

Bovine turbinate (BT) cells were used for all in vitro tests. Cells were grown to confluency in 25 cm² flasks in RMPI 1640 media supplemented with 10% v/v fetal bovine serum (FBS), 100 Units of penicillin (g/mL), 100 mg streptomycin/ mL and $5 \times 10^{-2}$ mM of 2-mercaptoethanol. After cell confluence was obtained, cells were maintained in the same media with reduced FBS (2% v/v). Cell cultures were incubated at 37 C. in a humidified atmosphere containing 5% carbon dioxide and 95% air.

For growth of the parasite, BT cell monolayers were infected with parasites and examined with an inverted microscope for the development of lesions (cytopathic effect, "CPE") or the presence of many extracellular merozoites. Once lesions were observed, or many extracellular parasites were present, the monolayer was scraped with the tip of a 5 mL pipette and 1 to 3 drops of the merozoite-containing fluid was transferred to two flasks of fresh BT cells. Merozoites of *S. neurona* were passaged in this manner every 5 to 10 days.

The assay used to determine the effectiveness of praziquantel was the Microtiter Monolayer Disruption Assay (MMDA). This assay was used to determine if the parasites or compound were toxic for BT cells. Flat bottomed 96-well microtiter plates were inoculated with BT cells and the resulting monolayers were used to determine the effect of praziquantel on merozoite production which is measured by CPE (cytopathic effect—plaque formation). Monolayers were inoculated with parasites (*S. neurona* at a count of 50,000/well). All wells were inoculated with the correct concentration of Praziquantel at 2 hours after infection of the monolayers. Untreated and uninfected monolayer wells served as parasite controls and uninfected agent treated BT cells served as toxicity controls. Each treatment was examined in replicates of 6. Each well was visually monitored daily and the assay was stopped when 90–100% of the untreated merozoite infected cells had lysed (90–100% CPE). All wells of the plates were rinsed in Phosphate Buffered Saline (PBS) and fixed in 100% methanol for 5 minutes after which they were stained in crystal violet solution. Areas of merozoite-induced destruction or BT cell death due to toxicity do not take up the crystal violet. An ELISA plate reader was used to quantitate the crystal violet incorporation and these data were used to determine the concentration of Praziquantel that inhibits destruction by 50% (Inhibitory Concentration$_{50}$ or IC$_{50}$). The data demonstrating inhibition are presented in Table 1. It is noted that as little as 10 μg/mL of Praziquantel provided 51% inhibition of cell destruction. Praziquantel at a concentration of 20 μg/mL produced a 69% inhibition of cell destruction. This indicates that Praziquantel would be effective for treatment of diseases caused by the coccidia known to be associated with neurological and abortigenic disease syndromes including diseases caused by *S. neurona, N. caninum, N. hugesi, T. gondii* and *I. Suis*. Additionally, Praziquantel was not toxic to the BT cells.

TABLE 1

In vitro Data on the Effect of Praziquantel on *Sarcocystis neurona*

| Organism | Percent Inhibition of Cell Destruction | | |
|---|---|---|---|
|  | 0 μg/mL | 10 μg/mL | 20 μg/mL |
| *Sarcocystis neurona* | 0% | 51% | 69% |

These data indicate that a dose of 2.5 to 10 mg/Kg would be neurologically-effective in treating a mammal suffering from disease caused by *Sarcocystis neurona*.

What is claimed is:

1. A method of therapeutically treating a diseased mammal suffering from a parasitic neurologic or abortigenic disease that is susceptible to being treated with a praziquantel compound, comprising administering to the mammal a composition of a pharmaceutically effective amount of praziquantel or a derivative thereof and a pharmaceutically acceptable carrier.

2. The method of claim 1 wherein the disease is caused by a coccidia.

3. The method of claim 2 wherein the coccidia is a member of the group consisting of Sarcocystis spp, Neospora spp, Toxoplasma spp and Isospora spp.

4. The method of claim 3 wherein the Sarcocystis spp is *Sarcocystis neurona*, the Neospora spp is *Neospora caninum* or *Neospora hugesi*, the Toxoplasma spp is *Toxoplasma gondii* and the Isospora spp is *Isospora suis*.

5. The method of claim 4 wherein the *Sarcocystis neurona* is the causative agent of Equine Protozoal Myeloencephalitis.

6. The method of claim 3 wherein the *Neospora caninum* is the causative agent of bovine or canine Neosporosis.

7. The method of claim 3 wherein the *Neospora hugesi* is the causative agent of Equine Protozoal Myeloencephalitis.

8. The method of claim 3 wherein the *Toxoplasma gondii* is the causative agent of Toxoplasma-associated abortion in mammals.

9. A method for treating a diseased mammal suffering from a parasitic neurologic or abortigenic disease that is susceptible to being treated with a praziquantel compound, comprising administering to the mammal a neurologically-effective or placentally-effective amount of praziquantel or a derivative thereof and a pharmaceutically acceptable carrier.

10. The method of metaphylactically treating mammals infected with a parasite that is a causative agent for a neurologic or abortigenic disease that is susceptible to being treated with a praziquantel compound, comprising administering thereto a methaphylactically-effective regimen of a composition of a pharmaceutically effective amount of the praziquantel compound or a derivative thereof and a pharmaceutically-acceptable carrier.

11. The method of claim 1 wherein the composition is administered in two or more intermittent doses.

12. The method of claim 1 wherein the composition is administered in a dose of about 1.0 and 100 mg/Kg.

13. The method of claim 2 wherein the composition is administered in a dose of about 1.0 and 50 mg/Kg.

14. The method of claim 1 wherein the composition is administered in a single high dose of greater than 50 mg/Kg.

* * * * *